(12) United States Patent
Kondo (10) Patent No.: US 11,871,894 B2
(45) Date of Patent: Jan. 16, 2024

(54) BIOLOGICAL INFORMATION MANAGEMENT SYSTEM

(71) Applicant: TATSUMI RYOKI CO., LTD, Tokyo (JP)

(72) Inventor: Toyoshi Kondo, Tokyo (JP)

(73) Assignee: TATSUMI RYOKI CO., LTD, Tokyo (JP)

(*) Notice: Subject to any disclaimer, the term of this patent is extended or adjusted under 35 U.S.C. 154(b) by 0 days.

(21) Appl. No.: 18/027,033

(22) PCT Filed: Oct. 28, 2021

(86) PCT No.: PCT/JP2021/039799
§ 371 (c)(1),
(2) Date: Mar. 17, 2023

(87) PCT Pub. No.: WO2022/113632
PCT Pub. Date: Jun. 2, 2022

(65) Prior Publication Data
US 2023/0270329 A1 Aug. 31, 2023

(30) Foreign Application Priority Data
Nov. 30, 2020 (JP) ................................ 2020-197894

(51) Int. Cl.
*A61B 5/00* (2006.01)
*A61B 5/11* (2006.01)

(52) U.S. Cl.
CPC .......... *A61B 5/0024* (2013.01); *A61B 5/1116* (2013.01); *A61B 5/681* (2013.01);
(Continued)

(58) Field of Classification Search
CPC ..... A61B 5/0024; A61B 5/1116; A61B 5/681; A61B 5/6823; A61B 5/7282; A61B 2562/0257
See application file for complete search history.

(56) References Cited

U.S. PATENT DOCUMENTS

| | | | | |
|---|---|---|---|---|
| 4,967,751 A | * | 11/1990 | Sterzer ................. | A61B 5/0507 600/407 |
| 2019/0053741 A1 | * | 2/2019 | Chaudhry ............ | A61B 5/6831 |
| 2020/0029852 A1 | * | 1/2020 | Sakai .................... | A61B 5/6892 |

FOREIGN PATENT DOCUMENTS

| | | |
|---|---|---|
| JP | 2017-58134 A | 3/2017 |
| JP | 2018-083018 A | 5/2018 |
| WO | 2018/189970 A1 | 10/2018 |

OTHER PUBLICATIONS

International Search Report issued in PCT/JP2021/039799 dated Nov. 30, 2021 with English Translation (5 pages).

(Continued)

*Primary Examiner* — Andrey Shostak
(74) *Attorney, Agent, or Firm* — Nakanishi IP Associates, LLC (57) ABSTRACT

A biological information management system includes a first information device including a first communication unit and a second information device including a second communication unit. The first information device is attached to a portion of a subject where a positional relationship with a reference position of the subject changes. The second information device is attached to the reference position or a portion where the positional relationship with the reference position changes. The first information device outputs biological abnormality/normality determination information based on a radio field intensity and a signal waveform of a radio wave received by transmission of a first signal between the first communication unit and the second communication unit when the first information device and the second information device have a predetermined positional relationship.

8 Claims, 3 Drawing Sheets

(52) U.S. Cl.
CPC .......... *A61B 5/6823* (2013.01); *A61B 5/7282* (2013.01); *A61B 2562/0257* (2013.01)

(56) References Cited

OTHER PUBLICATIONS

Written Opinion of International Searching Authority issued in PCT/JP2021/039799 dated Nov. 30, 2021 with English Translation (5 pages).
Decision to Grant Patent issued in Japanese Patent Application No. 2022-531454 dated Aug. 19, 2022, with English Translation (5 pages).
Notification of Reasons for Refusal issued in Japanese Patent Application No. 2022-531454 dated Jul. 8, 2022 with English Translation (6 pages).

* cited by examiner

BIOLOGICAL INFORMATION MANAGEMENT SYSTEM

TECHNICAL FIELD

The present invention relates to a biological information management system.

BACKGROUND ART

Conventionally, as in Patent Literature 1, there has been proposed a notification system that obtains biological information by a vital sensor or the like and transmits the biological information to an external information device or the like.

CITATION LIST

Patent Literature

Patent Literature 1: JP 2018-083018 A

SUMMARY OF INVENTION

Technical Problem

However, although information on a surface such as a body temperature of a subject can be obtained, information inside the subject cannot be sufficiently obtained.

Therefore, an object of the present invention is to provide a biological information management system and the like that can easily obtain the information inside the subject.

Solution to Problem

A biological information management system according to the present invention includes a first information device including a first communication unit and a second information device including a second communication unit.

The first information device is attached to a portion of a subject where a positional relationship with a reference position of the subject changes.

The second information device is attached to the reference position or a portion where the positional relationship with the reference position changes.

The first communication unit communicates with the second communication unit.

At least one of the first information device and the second information device performs at least one of recording and output of biological abnormality/normality determination information based on at least one of a radio field intensity and a signal waveform of a radio wave received by transmission of a first signal between the first communication unit and the second communication unit when the first information device and the second information device have a predetermined positional relationship.

The predetermined positional relationship is a state in which an inspection target region of the subject is located on a straight line connecting the first information device and the second information device between the first information device and the second information device.

The biological abnormality/normality determination information includes information on whether the inspection target region is normal.

When there is an abnormality in the inspection target region of the subject, such as head and heart, there is a high possibility that a degree of passage of the radio wave is different from normal.

Therefore, communication (transmission of the first signal) between the first information device and the second information device is performed in a state where said inspection target region is located between the first information device and the second information device, and it is possible to roughly determine whether said inspection target region is normal on the basis of the radio field intensity or the signal waveform, that is, to easily obtain the information inside the subject.

The first information device preferably includes a posture information detection unit.

A positional relationship between the first information device and the second information device is identified on the basis of information obtained by the posture information detection unit.

By obtaining the posture information of the subject using the posture information detection unit, it is easy to determine whether said inspection target region is located between the first information device and the second information device.

More preferably, at least one of the first information device and the second information device determines whether the first information device and the second information device have the predetermined positional relationship on the basis of information obtained by the posture information detection unit.

More preferably, the information on whether the inspection target region is normal includes at least one of a comparison result between the radio field intensity and a preset reference radio field intensity and a comparison result between the signal waveform and a preset reference signal waveform.

The reference radio field intensity is a radio field intensity reference value set in consideration of a degree of passage of a radio wave of the subject when the inspection target region of the subject is normal.

The reference signal waveform is a signal waveform reference value set in consideration of the degree of passage of the radio wave of the subject when the inspection target region of the subject is normal.

More preferably, an antenna used for communication of the first signal of the first communication unit includes a directional antenna.

An antenna used for communication of the first signal of the second communication unit includes an omnidirectional antenna having a small difference between a high gain direction and a low gain direction as compared with the antenna used for communication of the first signal of the first communication unit.

The antenna used for communication of the first signal of the first communication unit needs to transmit the first signal so as to pass through only a region including said inspection target region or receive the first signal having passed through only the region including said inspection target region, and the directional antenna is used.

The antenna used for communication of the first signal of the second communication unit needs to communicate with the first communication unit that can be located in various directions as viewed from the second communication unit, and the omnidirectional antenna is used.

Thus, it is possible to measure the radio field intensity or the like by using the first signal having passed through said region including the inspection target region without using the first signal not having passed through said inspection target region, and to accurately determine an abnormality in the inspection target region on the basis of a measurement result.

More preferably, the first information device is attached to an arm of the subject.

The second information device is provided at a portion of an outerwear worn on trunk of the subject.

A method according to the present invention is a method for obtaining information on whether an inspection target region is normal in a biological information management system including a first information device including a first communication unit and a second information device including a second communication unit.

The first information device is attached to a portion of a subject where a positional relationship with a reference position of the subject changes.

The second information device is attached to the reference position or a portion where the positional relationship with the reference position changes.

The first communication unit communicates with the second communication unit.

The method performs: a moving step of moving at least one of the first information device and the second information device to bring the first information device and the second information device into a predetermined positional relationship; and a communication step of performing at least one of recording and output of biological abnormality/normality determination information based on at least one of a radio field intensity and a signal waveform of a radio wave received by transmission of a first signal between the first communication unit and the second communication unit when the first information device and the second information device have the predetermined positional relationship.

The predetermined positional relationship is a state in which an inspection target region of the subject is located on a straight line connecting the first information device and the second information device between the first information device and the second information device.

The biological abnormality/normality determination information includes information on whether the inspection target region is normal.

A biological information management system according to the present invention includes a first information device including a first communication unit, a second information device including a second communication unit, and a tabulation device.

The first information device is attached to a portion of a subject where a positional relationship with a reference position of the subject changes.

The second information device is attached to the reference position or a portion where the positional relationship with the reference position changes.

The first communication unit communicates with the second communication unit.

The tabulation device communicates with at least one of the first communication unit and the second communication unit.

At least one of the first information device, the second information device, and the tabulation device performs at least one of recording and output of biological abnormality/normality determination information based on at least one of a radio field intensity and a signal waveform of a radio wave received by transmission of a first signal between the first communication unit and the second communication unit when the first information device and the second information device have a predetermined positional relationship.

The predetermined positional relationship is a state in which an inspection target region of the subject is located on a straight line connecting the first information device and the second information device between the first information device and the second information device.

The biological abnormality/normality determination information includes information on whether the inspection target region is normal.

Advantageous Effects of Invention

As described above, according to the present invention, it is possible to provide a biological information management system and the like that can easily obtain the information inside the subject.

DESCRIPTION OF EMBODIMENTS

Hereinafter, the present embodiment will be described with reference to the drawings.

Note that embodiments are not limited to the following embodiments. Further, contents described in one embodiment are similarly applied to other embodiments in principle. Furthermore, each embodiment and each modification can be appropriately combined.

(Biological Information Management System 1)

Figure 1:
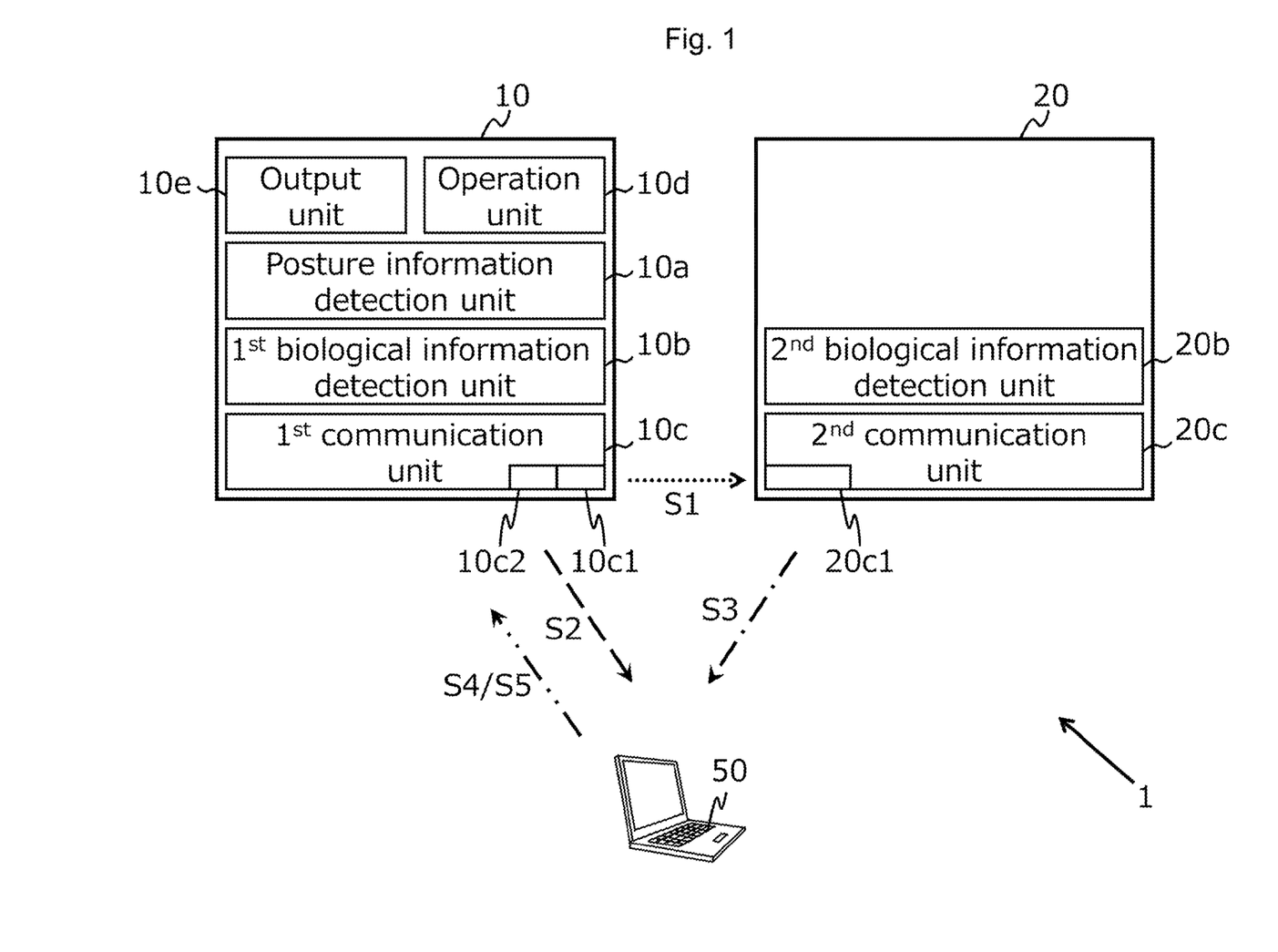
FIG. 1 is a schematic diagram illustrating a configuration of a biological information management system according to the present embodiment.
Figure 2:
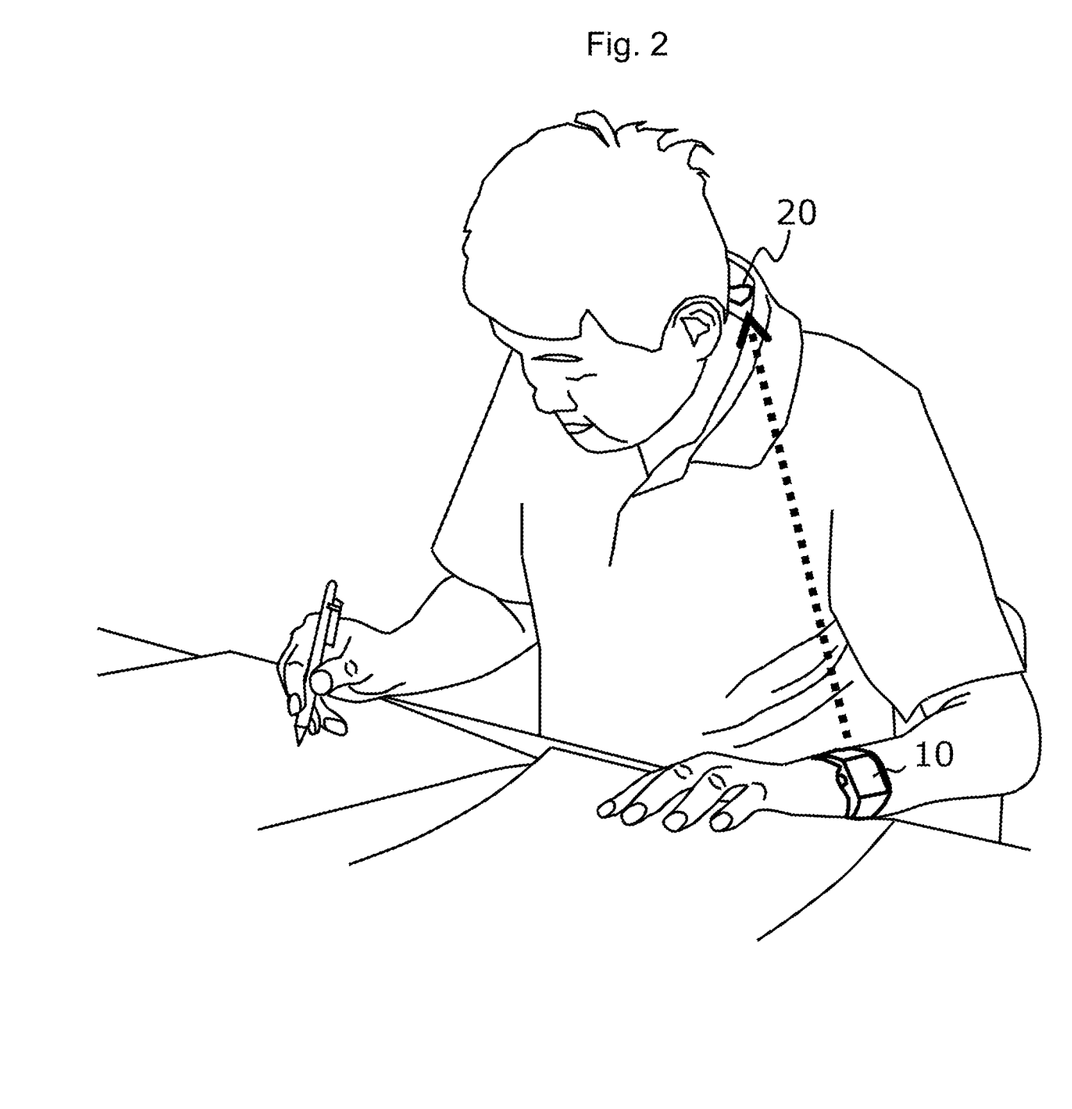
FIG. 2 is a perspective view of a first information device, a second information device, and a subject wearing the first information device and the second information device in a case where a first inspection target region (heart) is located between the first information device and the second information device.
Figure 3:
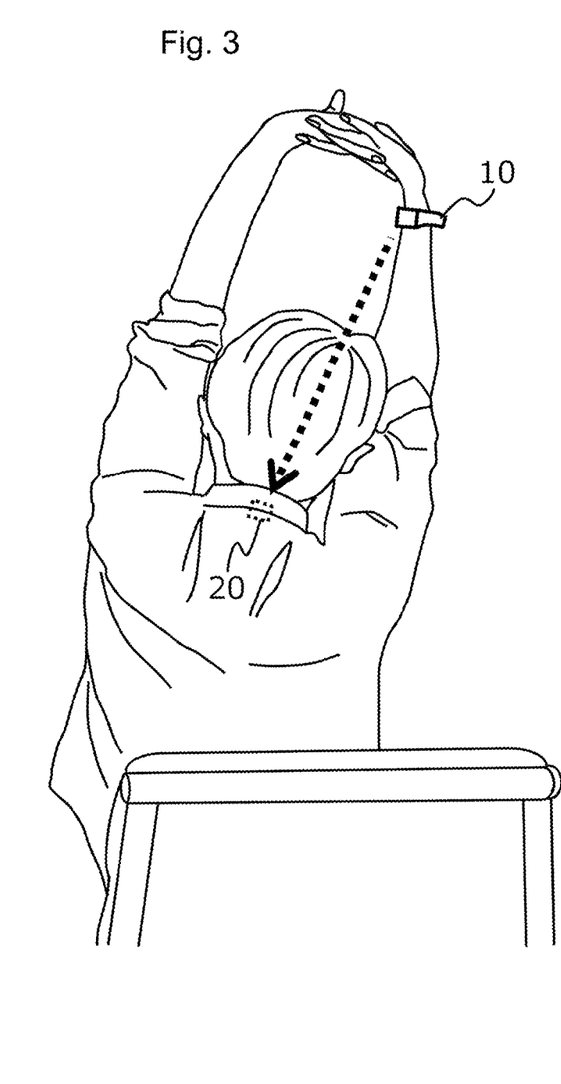
FIG. 3 is a perspective view of a first information device, a second information device, and a subject wearing the first information device and the second information device in a case where a second inspection target region (head) is located between the first information device and the second information device.

A biological management system 1 according to the present embodiment includes information devices (a first information device 10 and a second information device 20) and a tabulation device 50 (see FIGS. 1 to 3).

(Information Device)

The information devices (The first information device 10 and the second information device 20) are attached to a body of a person (subject), obtains posture information and biological information of the subject and surrounding information of the subject, and transmits obtained information and the like to the tabulation device 50.

Each of the first information device 10 and the second information device 20 has a shape that can be directly or indirectly attached to a part of a body of the subject.

At least one of the first information device 10 and the second information device 20 is attached to a portion where a positional relationship with a reference position (trunk) of the subject changes according to movement of the subject, such as an arm of the subject.

In the present embodiment, an example will be described in which the first information device 10 has a wristwatch-type housing and is wound around the arm of the subject, that is, the first information device 10 is attached to a portion where the positional relationship with the trunk of the subject changes.

Further, in the present embodiment, an example will be described in which the second information device 20 is provided at a portion (between a front collar and a back collar) of an outerwear worn on the trunk of the subject, that is, the second information device 20 is provided at a portion (the reference position) where the positional relationship with the trunk of the subject does not change. That is, clothes function as the second information device 20, or the clothes include the second information device 20.

In order to set various regions in the subject as the inspection target region, it is desirable that arrangement positions of the first information device 10 and the second information device 20 are determined such that a portion where the first information device 10 is attached is located at a position lower than the second information device 20 (see FIG. 2) or at a position higher than the second information device 20 (see FIG. 3) depending on posture of the subject.

(First Information Device 10)

The first information device 10 includes a posture information detection unit 10a, a first biological information detection unit 10b, a first communication unit 10c, an operation unit 10d, and an output unit 10e.

(Posture Information Detection Unit 10a)

The posture information detection unit 10a includes an acceleration sensor, a gyro sensor, and the like.

On the basis of information obtained by the posture information detection unit 10a, an orientation of a portion (here, the arm) of the subject where the first information device 10 is attached with respect to a reference portion (here, the trunk) of the subject, a positional relationship (a positional relationship between the first information device 10 and the second information device 20), and the like are identified.

In order to accurately identify the portion of the subject, it is desirable that an initial position is set via the operation unit 10d, and the orientation of the portion of the subject where the first information device 10 is attached with respect to the reference portion of the subject, the positional relationship, and the like are identified on the basis of information on said initial position and the information obtained by the posture information detection unit 10a. For example, it is considered that the initial position is a state in which the arm of the subject is extended downward.

(First Biological Information Detection Unit 10b)

The first biological information detection unit 10b includes a sensor that obtains biological information (body temperature, heart rate, or the like) of the portion of the subject where the first information device 10 is attached and obtains the surrounding information (humidity, temperature, or the like) of the subject.

The sensor of the first biological information detection unit 10b obtains the biological information and the like every first time t1 (for example, t1=1 hour).

The posture information detection unit 10a and the first biological information detection unit 10b may be configured integrally or separately.

(First Communication Unit 10c)

The first communication unit 10c transmits a first signal S1 to a second communication unit 20c of the second information device 20 (see dotted arrows in FIGS. 1 to 3).

(Content of First Signal S1)

The first signal S1 transmitted by the first communication unit 10c includes identification information of the first communication unit 10c.

(Directivity of Antenna for Transmitting First Signal S1)

An antenna (A first antenna) 10c1 for transmitting the first signal S1 of the first communication unit 10c desirably includes a directional antenna that transmits a strong radio wave in a direction in which the second communication unit 20c is located.

(Transmission Timing of First Signal S1)

When the first information device 10 and the second information device 20 attached to the subject have a predetermined positional relationship, communication between the first communication unit 10c and the second communication unit 20c (transmission of the first signal S1 from the first communication unit 10c to the second communication unit 20c) is performed for obtaining biological abnormality/normality determination information.

The predetermined positional relationship may be, for example, a state (see FIG. 2) in which heart of the subject is located on a straight line connecting the first information device 10 and the second information device 20 between the first information device 10 and the second information device 20 of the subject, or a state (see FIG. 3) in which a head of the subject is located on the straight line connecting the first information device 10 and the second information device 20 between the first information device 10 and the second information device 20 of the subject.

A determination as to whether the first information device 10 and the second information device 20 have the predetermined positional relationship is made by any one of the posture information detection unit 10a, the first communication unit 10c, and a control unit (not illustrated) on the basis of the information or the like obtained by the posture information detection unit 10a.

Further, the first communication unit 10c transmits a second signal S2 to the tabulation device 50 (see a broken-line arrow in FIG. 1).

(Content of Second Signal S2)

The second signal S2 transmitted by the first communication unit 10c includes the identification information of the first communication unit 10c, information (posture information) obtained by the posture information detection unit 10a, information (biological information and surrounding information) obtained by the first biological information detection unit 10b, date and time information when information was obtained, and the like.

The posture information included in the second signal S2 is, for example, a positional relationship of the first information device 10 with respect to the second information device 20. Specifically, the posture information included in the second signal S2 includes information about a region of the subject on the straight line connecting the first information device 10 and the second information device 20 between the first information device 10 and the second information device 20 (for example, that said region is the heart of the subject).

(Directivity of Antenna for Transmitting Second Signal S2)

An antenna (second antenna) 10c2 for transmitting the second signal S2 of the first communication unit 10c desirably includes an omnidirectional antenna having a small difference between a high gain direction and a low gain direction as compared with the antenna (first antenna) 10c1 for transmitting the first signal S1 of the first communication unit 10c.

The antenna 10c2 for transmitting the second signal S2 of the first communication unit 10c is also used for receiving a fourth signal S4 and a fifth signal S5 from the tabulation device 50 described later.

(Transmission Timing of Second Signal S2)

Transmission of the second signal S2 from the first communication unit 10c to the tabulation device 50 may be performed every second time t2 (for example, t2=1 second), or may be performed only when the first information device 10 and the second information device 20 attached to the subject have the predetermined positional relationship.

(Operation Unit 10d, Output Unit 10e)

The operation unit 10d and the output unit 10e are used for setting the initial position of the first information device 10, an operation of starting the transmission of the first signal S1 from the first communication unit 10c to the second communication unit 20c for obtaining the biological abnormality/normality determination information, and the like.

The output unit 10e of the first information device 10 outputs biological abnormality information, biological normality information, and the like, which will be described later, by voice or video.

(Second Information Device 20)

The second information device 20 includes a second biological information detection unit 20b and the second communication unit 20c.

(Second Biological Information Detection Unit 20b)

The second biological information detection unit 20b includes a sensor that obtains biological information (body temperature, heart rate, or the like) of a portion (here, a neck) of the subject where the second information device 20 is attached and obtains the surrounding information (humidity, temperature, or the like) of the subject.

The sensor of the second biological information detection unit 20b obtains the biological information and the like every first time t1.

(Second Communication Unit 20c)

The second communication unit 20c receives the first signal S1 from the first communication unit 10c.

The second communication unit 20c transmits a third signal S3 to the tabulation device 50 (see a one-dot chain line arrow in FIG. 1).

(Content of Third Signal S3)

The third signal S3 transmitted by the second communication unit 20c includes identification information of the second communication unit 20c, information (biological information and surrounding information) obtained by the second biological information detection unit 20b, date and time information when information was obtained, information (reception information of the first signal S1) obtained by the second communication unit 20c, and the like.

(Reception Information of First Signal S1)

The reception information of the first signal S1 includes information on the radio field intensity and the signal waveform of the first signal S1 received by the second communication unit 20c, a comparison result between said radio field intensity and a preset reference radio field intensity, and a comparison result between said signal waveform and a preset reference signal waveform.

The reference radio field intensity is a radio field intensity reference value set in consideration of a degree of passage of a radio wave of the subject when the region (inspection target region) of the subject which is located on the straight line connecting the first information device 10 and the second information device 20 between the first information device 10 and the second information device 20 is normal (healthy body).

The reference signal waveform is a signal waveform reference value set in consideration of the degree of passage of the radio wave of the subject when the region (inspection target region) of the subject which is located on the straight line connecting the first information device 10 and the second information device 20 between the first information device 10 and the second information device 20 is normal.

The radio field intensity reference value and the signal waveform reference value may be calculated from a general numerical value of the same age and gender as the subject, or may be calculated from an average value of past data (the radio field intensity and the signal waveform) of the subject.

When the first signal S1 is transmitted under the condition where a first inspection target region (heart) of the subject is located on the straight line connecting the first information device 10 and the second information device 20 between the first information device 10 and the second information device 20 and the first signal S1 is transmitted under the condition where a second inspection target region (head) of the subject is located on the straight line connecting the first information device 10 and the second information device 20 between the first information device 10 and the second information device 20, two types of reference radio field intensity and reference signal waveform are provided. One corresponds to the first inspection target region and the other corresponds to the second inspection target region.

(Directivity of Antenna for Receiving First Signal S1 and Antenna for Transmitting Third Signal S3)

An antenna 20c1 of the second communication unit 20c, that is, an antenna for receiving the first signal S1 and for transmitting the third signal S3 desirably includes an omni-directional antenna having a small difference between a high gain direction and a low gain direction as compared with the antenna (first antenna) 10c1 for transmitting the first signal S1 of the first communication unit 10c.

(Transmission Timing of Third Signal S3)

Transmission of the third signal S3 from the second communication unit 20c to the tabulation device 50 may be performed every second time t2, or may be performed only when the first information device 10 and the second information device 20 attached to the subject have the predetermined positional relationship (when the first signal S1 is received).

(Wireless Communication Means Such as First Communication Unit 10c)

A wireless communication means of wireless communication (transmission of the first signal S1) performed between the first communication unit 10c (e.g., including a transmitter and a receiver) and the second communication unit 20c (e.g., including a transmitter and a receiver), a wireless communication means of wireless communication (transmission of the second signal S2) performed between the first communication unit 10c and the tabulation device 50, and a wireless communication means of wireless communication (transmission of the third signal S3) performed between the second communication unit 20c and the tabulation device 50 have communication scheme of an RF tag or are means for transmitting identification information of themselves to the outside while said wireless communication means is turned on, and may be IEEE 802.15.1 (Bluetooth (registered trademark)), IEEE 802.11 (wireless LAN), or the like.

(Tabulation Device 50)

The tabulation device 50 receives the second signal S2 from the first communication unit 10c.

The tabulation device 50 receives the third signal S3 from the second communication unit 20c.

The tabulation device 50 determines whether a health condition (the inspection target region) of the subject is normal or abnormal on the basis of the second signal S2 and the third signal S3.

For example, when a difference between said radio field intensity and the preset reference radio field intensity is larger than a radio field intensity difference threshold and/or a difference between said signal waveform and the preset reference signal waveform is larger than a signal waveform difference threshold, it is determined that the health condition of the subject is abnormal.

When the tabulation device 50 determines that the health condition of the subject is abnormal, it transmits the fourth signal S4 to the first communication unit 10c (see a two-dot chain line arrow in FIG. 1).

(Content of Fourth Signal S4)

The fourth signal S4 transmitted by the tabulation device 50 includes identification information of the tabulation device 50, information (biological abnormality information) indicating that the health condition of the subject (the inspection target region of the subject) is different from a normal state from the degree of passage of the radio wave of the first signal S1, and the like.

(Transmission of Fifth Signal S5)

When the tabulation device 50 determines that the health condition of the subject is normal, it may transmit the fifth signal S5 to the first communication unit 10c (see the two-dot chain line arrow in FIG. 1).

The fifth signal S5 transmitted by the tabulation device 50 includes the identification information of the tabulation device 50, information (biological normality information) indicating that the health condition of the subject (the inspection target region of the subject) is in a normal state from the degree of passage of the radio wave of the first signal S1, and the like.

The fourth signal S4 and the fifth signal S5 may be transmitted not only to the first communication unit 10c but also to an external device (not illustrated).

Further, the biological abnormality/normality determination information (the biological abnormality information and the biological normality information) may be recorded in any one of the first information device 10, the second information device 20, and the tabulation device 50.

(Operation Procedure)

Next, a procedure for outputting the biological abnormality/normality determination information to the output unit 10e of the first information device 10 will be described.

The first information device 10 is attached to the arm of the subject, and the outerwear including the second information device 20 is worn on the trunk of the subject, in advance.

(Moving Step)

The arm of the subject is moved to move the first information device 10 such that the first information device 10 and the second information device 20 have the predetermined positional relationship, that is, such that the inspection target region of the subject is located on the straight line connecting the first information device 10 and the second information device 20 between the first information device 10 and the second information device 20 (moving step).

In a case where the inspection target region is the first inspection target region (heart), for example, as illustrated in FIG. 2, when the subject sits on a chair and puts the arm on a desk, the inspection target region is located on the straight line connecting the first information device 10 and the second information device 20 between the first information device 10 and the second information device 20.

In a case where the inspection target region is the second inspection target region (head), for example, as illustrated in FIG. 3, when the subject extends the arm upward, the inspection target region is located on the straight line connecting the first information device 10 and the second information device 20 between the first information device 10 and the second information device 20.

(Communication Step)

Next, the biological abnormality/normality determination information is generated on the basis of at least one of the signal waveform and the radio field intensity of the radio wave received by transmission of the first signal S1 from the first communication unit 10c to the second communication unit 20c when the first information device 10 and the second information device 20 have said predetermined positional relationship, and at least one of recording and output of said biological abnormality/normality determination information is performed (communication step).

Specifically, when the first information device 10 and the second information device 20 have said predetermined positional relationship, the first communication unit 10c transmits the first signal S1 to the second communication unit 20c.

The first signal S1 reaches the second communication unit 20c through the inspection target region.

The second communication unit 20c receives the first signal S1, generates the reception information of first signal S1 on the basis of the radio field intensity and the signal waveform, and transmits the reception information as the third signal S3 to the tabulation device 50.

Further, the first communication unit 10c transmits the second signal S2 to the tabulation device 50.

The tabulation device 50 receives the second signal S2 and the third signal S3, determines whether the inspection target region is normal or abnormal on the basis of these signals, and generates the biological abnormality/normality determination information.

The tabulation device 50 transmits the biological abnormality information (fourth signal S4) or the biological normality information (fifth signal S5) included in the biological abnormality/normality determination information to the first communication unit 10c.

The output unit 10e of the first information device 10 outputs the biological abnormality information, or the biological normality information.

Note that the output unit 10e of the first information device 10 may output the biological abnormality information only when the inspection target region is abnormal, and may not output the biological normality information when the inspection target region is normal.

(Effect of Performing Communication with Subject Sandwiched)

When there is an abnormality in the inspection target region of the subject, such as head and heart, there is a high possibility that the degree of passage of the radio wave is different from normal (for example, the radio field intensity is reduced, or the signal waveform is distorted).

Therefore, communication (transmission of the first signal S1) between the first information device 10 and the second information device 20 is performed in a state where said inspection target region is located between the first information device 10 and the second information device 20, and it is possible to roughly determine whether said inspection target region is normal on the basis of the radio field intensity or the signal waveform, that is, to easily obtain the information inside the subject.

(Effect of Detecting Posture Information)

By obtaining the posture information of the subject using the posture information detection unit 10a, it is easy to determine whether said inspection target region is located between the first information device 10 and the second information device 20.

(Effect of Using Antenna with Different Directivity)

The antenna (first antenna 10c1) used for communication of the first signal S1 of the first communication unit 10c needs to transmit and receive the first signal S1 so as to pass through only a region including said inspection target region, and the directional antenna is used.

The antenna 20c1 used for communication of the first signal S1 of the second communication unit 20c needs to communicate with the first communication unit 10c that can be located in various directions as viewed from the second communication unit 20c, and the omnidirectional antenna is used.

Thus, it is possible to measure the radio field intensity or the like by using the first signal S1 having passed through the region including said inspection target region without using the first signal S1 not having passed through said inspection target region, and to accurately determine an abnormality in said inspection target region on the basis of a measurement result.

(Effect of Wearing First Information Device 10 on Arm)

By lowering the arm downward, the first information device 10 is positioned downward, and by raising the arm upward, the first information device 10 is positioned upward.

Therefore, it is possible to easily establish a positional relationship with the second information device 20 so as to sandwich the inspection target region such as head and heart.

(Application Example of Information Used for Generating Biological Abnormality/Normality Determination Information)

In the present embodiment, an example has been described in which the biological abnormality/normality determination information (the biological abnormality information and the biological normality information) is generated on the basis of at least one of the signal waveform and the radio field intensity of the first signal S1.

However, the biological abnormality/normality determination information may be generated in consideration of other information as well.

Specifically, a determination as to whether the inspection target region is abnormal may be made on the basis of the information (biological information and surrounding information) obtained by the first biological information detection unit 10b, and the information (biological information and surrounding information) obtained by the second biological information detection unit 20b, at least one of the signal waveform and the radio field intensity of the first signal S1.

For example, when the difference between said radio field intensity and the preset reference radio field intensity is larger than the radio field intensity difference threshold and/or the difference between said signal waveform and the preset reference signal waveform is larger than the signal waveform difference threshold, and when a difference between the body temperature included in the biological information obtained by the first biological information detection unit 10b and the body temperature included in the biological information obtained by the second biological information detection unit 20b is larger than a body temperature difference threshold, it is determined that the health condition of the subject is abnormal.

(Application Example of Transmission Direction of First Signal S1)

In the present embodiment, an example in which the first signal S1 is transmitted from the first communication unit 10c to the second communication unit 20c has been described.

However, the first signal S1 may be transmitted from the second communication unit 20c to the first communication unit 10c.

In this case, a signal for instructing the transmission of the first signal S1 is transmitted from the first communication unit 10c to the second communication unit 20c on the basis of the information or the like obtained by the posture information detection unit 10a.

(Application Example of Entity for Abnormality Determination of Health Condition of Subject)

In the present embodiment, an example has been described in which the tabulation device 50 generates the biological abnormality/normality determination information (the biological abnormality information and the biological normality information) on the basis of at least one of the signal waveform and the radio field intensity of the first signal S1 and causes the first information device 10 to output the biological abnormality/normality determination information.

However, the biological abnormality/normality determination information may be generated by the first information device 10 or the second information device 20.

That is, a determination as to whether the inspection target region is normal or abnormal from the degree of passage of the radio wave of the first signal S1 may be made by the tabulation device 50, or may be made by the first information device 10 or the second information device 20.

When the first information device 10 or the second information device 20 makes said determination, the tabulation device 50 may be omitted.

(Application Example 1 of Transmission Timing of First Signal S1)

In the present embodiment, an embodiment has been described in which the transmission of the first signal S1 for obtaining the biological abnormality/normality determination information is automatically started when it is determined that the first information device 10 and the second information device 20 have the predetermined positional relationship on the basis of the information or the like obtained by the posture information detection unit 10a.

However, the transmission of the first signal S1 may be started on the basis of an operation of a user such as the subject.

In this case, the first signal S1 is transmitted from the first communication unit 10c to the second communication unit 20c for obtaining the biological abnormality/normality determination information by operating the operation unit 10d when it is determined that the first information device 10 and the second information device 20 attached to the subject have the predetermined positional relationship of the subject or before a third time t3 (for example, t3=3 seconds) when said predetermined positional relationship is established, by visual observation or the like.

In this case, the posture information detection unit 10a may be omitted.

(Application Example 2 of Transmission Timing of First Signal S1)

In the present embodiment, an embodiment has been described in which the first signal S1 is transmitted only when a predetermined condition is satisfied, such as when the first information device 10 and the second information device 20 have the predetermined positional relationship.

However, the first signal S1 may be transmitted from the second communication unit 20c to the first communication unit 10c every second time t2.

In this case, among the first signal S1 transmitted from the first communication unit 10c to the second communication unit 20c, that in a time zone in which the predetermined positional relationship is established is included in the third signal S3 as the reception information of the first signal S1.

Alternatively, among the third signal S3 transmitted from the second communication unit 20c to the tabulation device 50, on the basis of that in the time zone in which the predetermined positional relationship is established, the biological abnormality/normality determination information is generated.

(Application Example of Attachment Position of First Information Device 10)

In the present embodiment, an example in which the first information device 10 is attached to the arm of the subject like a wristwatch has been described.

However, an attachment position of the first information device 10 is not limited to the arm.

For example, the first information device 10 may be attached to a leg, a head, or the like.

(Application Example 1 of Attachment Position of Second Information Device 20)

In the present embodiment, an example has been described in which the second information device 20 is provided between the front collar and the back collar of the clothes (outerwear).

However, the attachment position of the second information device 20 is not limited to the vicinity of the neck of the subject.

For example, the second information device 20 may be attached to the subject by being wound around a belly like a belt.

(Application Example 2 of Attachment Position of Second Information Device 20)

In the present embodiment, an example has been described in which the second information device 20 is provided at the portion (the reference position) where the positional relationship with the trunk of the subject does not change.

However, similarly to the first information device 10, the second information device 20 may be provided at a portion away from said reference position and where the positional relationship with said reference position changes according to the movement of the subject.

For example, the second information device 20 may be attached to the arm of the subject, which is an arm (for example, a left arm) opposite to the arm (for example, the right arm) to which the first information device 10 is attached.

Although some embodiments of the present invention have been described, these embodiments have been presented as examples, and are not intended to limit the scope of the invention. These embodiments can be implemented in various other forms, and various omissions, substitutions, and changes can be made without departing from the gist of the invention. These embodiments and modifications thereof are included in the scope and gist of the invention and are included in the invention described in the claims and the equivalent scope thereof.

REFERENCE SIGNS LIST

1 Biological information management system
10 First information device
10a Posture information detection unit
10b First biological information detection unit
10c First communication unit
10c1 First antenna of first communication unit
10c2 Second antenna of first communication unit
10d Operation unit
10e Output unit
20 Second information device
20b Second biological information detection unit
20c Second communication unit
20c1 Antenna of second communication unit
50 Tabulation device
S1 First signal (from first information device to second information device)
S2 Second signal (from first information device to tabulation device)
S3 Third signal (from second information device to tabulation device)
t1 First time (Biological information obtaining interval of sensor)
t2 Second time (Transmission interval of second signal or the like)
t3 Third time (First signal transmission timing for obtaining biological abnormality/normality determination information)

The invention claimed is:

1. A biological information management system comprising:
a first information device including a first communication device that includes a transmitter and a receiver; and
a second information device including a second communication device that includes a transmitter and a receiver, wherein
the first information device is configured to be attached to a portion of a subject where a positional relationship with a reference position of the subject changes,
the second information device is configured to be attached to the reference position or a portion where the positional relationship with the reference position changes,
the first communication device communicates with the second communication device,
at least one of the first information device and the second information device performs at least one of recording and outputting biological information based on at least one of a radio field intensity and a signal waveform of a radio wave of a first signal between the first communication device and the second communication device when the first information device and the second information device have a predetermined positional relationship,
the predetermined positional relationship is a state in which an inspection target region of the subject is located on a straight line connecting the first information device and the second information device between the first information device and the second information device, and
the biological information includes information on the inspection target region.

2. The biological information management system according to claim 1, wherein
the first information device includes a posture detector, and
a positional relationship between the first information device and the second information device is identified on the basis of information obtained by the posture detector.

3. The biological information management system according to claim 2, wherein at least one of the first information device and the second information device determines whether the first information device and the second information device have the predetermined positional relationship on the basis of the information obtained by the posture detector.

4. The biological information management system according to claim 1, wherein
the information on the inspection target region includes at least one of a comparison result between the radio field intensity and a preset reference radio field intensity and a comparison result between the signal waveform and a preset reference signal waveform,
the reference radio field intensity is a radio field intensity reference value set in consideration of a degree of passage of a radio wave of the subject, and
the reference signal waveform is a signal waveform reference value set in consideration of the degree of passage of the radio wave of the subject.

5. The biological information management system according to claim 1, wherein
an antenna used for communication of the first signal of the first communication device includes a directional antenna, and
an antenna used for communication of the first signal of the second communication device includes an omnidirectional antenna.

6. The biological information management system according to claim 1, wherein
the first information device is configured to be attached to an arm of the subject, and
the second information device is configured to be provided at a portion of an outerwear worn on a trunk of the subject.

7. A method for obtaining information on an inspection target region in a biological information management system including a first information device including a first communication device that includes a transmitter and a receiver and a second information device including a second communication device that includes a transmitter and a receiver, wherein
the first information device is configured to be attached to a portion of a subject where a positional relationship with a reference position of the subject changes,
the second information device is configured to be attached to the reference position or a portion where the positional relationship with the reference position changes, and
the first communication device communicates with the second communication device,
the method comprises:
a moving step of moving at least one of the first information device and the second information device to bring the first information device and the second information device into a predetermined positional relationship; and
a communication step of performing at least one of recording and outputting biological information based on at least one of a radio field intensity and a signal waveform of a radio wave of a first signal between the first communication device and the second communication device when the first information device and the second information device have the predetermined positional relationship,
the predetermined positional relationship is a state in which an inspection target region of the subject is located on a straight line connecting the first information device and the second information device between the first information device and the second information device, and
the biological information includes information on the inspection target region.

8. A biological information management system comprising:
a first information device including a first communication device that includes a transmitter and a receiver;
a second information device including a second communication device that includes a transmitter and a receiver; and
a tabulation device that includes a transmitter and a receiver, wherein
the first information device is configured to be attached to a portion of a subject where a positional relationship with a reference position of the subject changes,
the second information device is configured to be attached to the reference position or a portion where the positional relationship with the reference position changes,
the first communication device communicates with the second communication device,
the tabulation device communicates with at least one of the first communication device and the second communication device,
at least one of the first information device, the second information device, and the tabulation device performs at least one of recording and outputting biological information based on at least one of a radio field intensity and a signal waveform of a radio wave of a first signal between the first communication device and the second communication device when the first information device and the second information device have a predetermined positional relationship,
the predetermined positional relationship is a state in which an inspection target region of the subject is located on a straight line connecting the first information device and the second information device between the first information device and the second information device, and
the biological information includes information on the inspection target region.

* * * * *